(12) United States Patent
Eisermann et al.

(10) Patent No.: US 8,211,175 B2
(45) Date of Patent: Jul. 3, 2012

(54) ARTICULAR DISC PROSTHESIS AND METHOD FOR IMPLANTING THE SAME

(75) Inventors: Lukas Eisermann, Memphis, TN (US); Eddie F. Ray, III, Collierville, TN (US)

(73) Assignee: Warsaw Orthopedic, Warsaw, IN (US)

( * ) Notice: Subject to any disclaimer, the term of this patent is extended or adjusted under 35 U.S.C. 154(b) by 1270 days.

(21) Appl. No.: 11/542,673

(22) Filed: Oct. 3, 2006

(65) Prior Publication Data
US 2007/0088440 A1 Apr. 19, 2007

Related U.S. Application Data

(63) Continuation of application No. 10/412,700, filed on Apr. 11, 2003, now Pat. No. 7,179,294.

(60) Provisional application No. 60/375,354, filed on Apr. 25, 2002.

(51) Int. Cl.
*A61F 2/44* (2006.01)
(52) U.S. Cl. ............... 623/17.14; 623/17.11; 623/17.15; 623/17.16
(58) Field of Classification Search ..... 623/17.11–17.16
See application file for complete search history.

(56) References Cited

U.S. PATENT DOCUMENTS

| | | | |
|---|---|---|---|
| 4,759,766 A | 7/1988 | Buettner-Janz et al. |
| 4,997,432 A | 3/1991 | Keller |
| 5,246,458 A | 9/1993 | Graham |
| 5,258,031 A | 11/1993 | Salib et al. |
| 5,306,307 A | 4/1994 | Senter et al. |
| 5,306,308 A | 4/1994 | Gross et al. |
| 5,314,477 A | 5/1994 | Marnay |
| 5,401,269 A | 3/1995 | Buttner-Janz et al. |
| 5,425,773 A | 6/1995 | Boyd et al. |
| 5,507,816 A | 4/1996 | Bullivant |
| 5,534,029 A | 7/1996 | Shima |
| 5,556,431 A | 9/1996 | Buttner-Janz |
| 5,562,738 A | 10/1996 | Boyd et al. |
| 5,674,296 A | 10/1997 | Bryan et al. |
| 5,676,701 A | 10/1997 | Yuan et al. |
| 5,683,394 A | 11/1997 | Rinner |
| 5,683,465 A | 11/1997 | Shinn et al. |
| 5,755,796 A | 5/1998 | Ibo et al. |

(Continued)

FOREIGN PATENT DOCUMENTS

DE 28 04 936 A 8/1979

(Continued)

*Primary Examiner* — Eduardo C Robert
*Assistant Examiner* — Julianna N Harvey (57) ABSTRACT

An articular disc prosthesis and method of implanting the same within an intervertebral space between adjacent vertebral bodies. The prosthesis includes a pair of articular components and an articular ball disposed therebetween. Each of the articular components includes an outer shell portion and a removable inner insert portion. The insert portion includes a concave articular surface sized and shaped to receive a portion of the articular ball to provide articulating motion between the articular components. The outer shell portion includes a central hemi-cylindrical portion, a pair of laterally extending flanges, and an axially extending lip. Following removal of the natural intervertebral disc, a pair of hemi-cylindrical recesses are formed along a central region of the adjacent vertebral bodies to a predetermined depth. The prosthesis is implanted within the prepared disc space by axially displacing the hemi-cylindrical central portions of the articular components along the hemi-cylindrical recesses in the vertebral bodies. The lateral flanges and the axial lip of the articular components bear against the endplates of the adjacent vertebral bodies to stabilize the prosthesis and to prevent subsidence.

16 Claims, 6 Drawing Sheets

U.S. PATENT DOCUMENTS

| | | |
|---|---|---|
| 5,782,832 A | 7/1998 | Larsen et al. |
| 5,865,846 A | 2/1999 | Bryan et al. |
| 5,888,226 A * | 3/1999 | Rogozinski ............... 623/17.16 |
| 5,895,428 A | 4/1999 | Berry |
| 5,899,941 A | 5/1999 | Nishijima et al. |
| 6,001,130 A | 12/1999 | Bryan et al. |
| 6,019,792 A | 2/2000 | Cauthen |
| 6,063,121 A | 5/2000 | Xavier et al. |
| 6,179,874 B1 | 1/2001 | Cauthen |
| 6,251,140 B1 * | 6/2001 | Marino et al. ............. 623/17.16 |
| 6,383,221 B1 | 5/2002 | Scarborough et al. |
| 6,517,580 B1 | 2/2003 | Ramadan et al. |
| 6,682,562 B2 | 1/2004 | Viart et al. |
| 6,685,742 B1 | 2/2004 | Jackson |

FOREIGN PATENT DOCUMENTS

| | | |
|---|---|---|
| EP | 0 560 141 B1 | 10/1996 |
| EP | 0 820 740 A1 | 1/1998 |
| EP | 0 560 140 B1 | 5/1998 |
| EP | 0 955 021 A | 11/1999 |
| EP | 0 747 025 B1 | 9/2002 |
| FR | 2 801 782 A | 6/2001 |
| FR | 2 805 985 A | 9/2001 |
| WO | WO 99/00074 | 1/1999 |
| WO | WO 99/05995 | 2/1999 |
| WO | WO 99/53871 | 10/1999 |
| WO | WO 00/42954 A2 | 7/2000 |
| WO | WO 00/42954 A3 | 7/2000 |
| WO | WO 01/01893 | 1/2001 |
| WO | WO 01/64140 | 9/2001 |

* cited by examiner

ARTICULAR DISC PROSTHESIS AND METHOD FOR IMPLANTING THE SAME

CROSS REFERENCE TO RELATED APPLICATIONS

The present application is a continuation of U.S. patent application Ser. No. 10/412,700 filed on Apr. 11, 2003, now issued as U.S. Pat. No. 7,179,294, which claims the benefit of U.S. Provisional Application Ser. No. 60/375,354 filed on Apr. 25, 2002, the contents of which are hereby incorporated by reference in their entirety.

FIELD OF THE INVENTION

The present invention relates generally to the field of spinal implants, and more particularly relates to an articular disc prosthesis and method of implantation for use in the total or partial replacement of a natural intervertebral disc.

BACKGROUND OF THE INVENTION

In the treatment of diseases, injuries or malformations affecting spinal motion segments, and especially those affecting disc tissue, it has long been known to remove some or all of a degenerated, ruptured or otherwise failing disc. In cases involving intervertebral disc tissue that has been removed or is otherwise absent from a spinal motion segment, corrective measures are indicated to insure the proper spacing of the vertebrae formerly separated by the removed disc tissue.

In some instances, the two adjacent vertebrae are fused together using transplanted bone tissue, an artificial fusion component, or other compositions or devices. Spinal fusion procedures, however, have raised concerns in the medical community that the bio-mechanical rigidity of intervertebral fusion may predispose neighboring spinal motion segments to rapid deterioration. More specifically, unlike a natural intervertebral disc, spinal fusion prevents the fused vertebrae from pivoting and rotating with respect to one another. Such lack of mobility tends to increase stresses on adjacent spinal motion segments. Additionally, several conditions may develop within adjacent spinal motion segments, including disc degeneration, disc herniation, instability, spinal stenosis, spondylosis and facet joint arthritis. Consequently, many patients may require additional disc removal and/or another type of surgical procedure as a result of spinal fusion. Alternatives to spinal fusion are therefore desirable.

Several different types of intervertebral disc arthroplasty devices have been proposed for preventing the collapse of the intervertebral space between adjacent vertebrae while maintaining a certain degree of stability and range of pivotal and rotational motion therebetween. Such devices typically include two or more articular components that are attached to respective upper and lower vertebrae. The articular components are anchored to the upper and lower vertebrae by a number of methods, including the use of bone screws that pass through corresponding openings in each of the elements and thread into vertebral bone, and/or by the inclusion of spikes or teeth that penetrate the vertebral endplates to inhibit migration or expulsion of the device. The articular components are typically configured to allow the elements, and correspondingly the adjacent vertebrae, to pivot and/or rotate relative to one another.

As discussed above, prior intervertebral disc arthroplasty devices are relatively difficult to implant between adjacent vertebrae. To implant such devices, the adjacent vertebrae are spread apart a distance that is somewhat greater than the normal distance separating the vertebrae so that the device can be maneuvered between the vertebrae and the anchors can be engaged to the vertebral endplates. Such an operation presents a risk of injury to the vertebrae caused by misplacement and/or scratching of the vertebral endplates or other tissue by the anchors. Such operation also presents a risk of injury resulting from over-distraction of the intervertebral space. As also discussed above, other types of prior arthroplasty devices require the threading of bone screws or another type of fastener into the adjacent vertebrae. However, this type of anchoring method requires precise placement and orientation of the bone screws to provide adequate anchoring and to avoid injury to adjacent tissue or vertebral structures. Moreover, prior methods of implanting arthroplasty devices do not reliably position the device at the proper location within the intervertebral disc space.

The articular components associated with prior arthroplasty devices are also prone to wear, particularly in cases where the abutting surface area of the articular joint is relatively small. Generally, as the abutting surface area of an articular joint is reduced, contact stress is correspondingly increased which may reduce the overall life of the joint. As a result, worn out components must be periodically replaced to avoid malfunctioning or potential breakage of the arthroplasty device.

Thus, there is a general need in the industry to provide an improved articular disc prosthesis and a method of implanting the same than is currently available within the industry. The present invention meets this need and provides other benefits and advantages in a novel and unobvious manner.

SUMMARY OF THE INVENTION

The present invention relates generally to an articular disc prosthesis and a method of implanting the same. While the actual nature of the invention covered herein can only be determined with reference to the claims appended hereto, certain forms of the invention that are characteristic of the preferred embodiments disclosed herein are described briefly as follows.

One form of the present invention is directed to an articular disc prosthesis, including a first articular component having a first bearing surface adapted to engage a first vertebra, and a second articular component having second bearing surface adapted to engage a second vertebra, with the first and second bearing surfaces defining a space therebetween. At least one of the first and second articular components includes a concave articular surface that cooperates with a corresponding convex articular surface to provide articulating motion between the first and second articular components, with at least a portion of the concave articular surface extending beyond the space between the first and second bearing surfaces.

Another form of the present invention is directed to an articular disc prosthesis for replacement of a natural intervertebral disc, including a first articular component defining a first concave articular surface, a second articular component defining a second concave articular surface, and an articular ball positioned between the first and second concave articular surfaces to provide articulating motion between the first and second articular components, and wherein the articular ball has a diameter greater than a height of the natural intervertebral disc.

Another form of the present invention is directed to an articular disc prosthesis, including a first articular component adapted to engage a first vertebra, a second articular component adapted to engage a second vertebra, and wherein each of the first and second articular components extends along an axis and includes a central axial portion defining a convex lateral curvature and a pair of flanges extending laterally from the central axial portion in generally opposite directions.

Another form of the present invention is directed to an articular disc prosthesis, including first and second modular articular components, with each of the modular articular components having an outer shell portion configured to engage a corresponding one of first and second vertebrae, and an inner insert portion removably engaged with the outer shell portion. The inner insert portion includes an articular surface cooperating with a corresponding articular surface to provide articulating motion between the first and second modular articular components.

Another form of the present invention is directed to a method of implanting an articular disc prosthesis between first and second vertebrae, including providing an articular disc prosthesis having a first articular component adapted to engage a first vertebra and a second articular component adapted to engage a second vertebra, with each of the first and second articular components extending along an axis and including a central axial portion defining a convex lateral curvature and a pair of flanges extending laterally from the central axial portion in generally opposite directions. The method further includes removing at least a portion of a natural interverterbral disc from between the first and second vertebrae to form an intervertebral space, forming an elongate recess along a central region of each of the first and second vertebrae, and implanting the articular disc prosthesis within the intervertebral space by inserting the central axial portions of the first and second articular components within the elongate recesses formed along the first and second vertebrae.

It is one object of the present invention to provide an improved articular disc prosthesis. It is another object of the present invention to provide an improved method of implanting an articular disc prosthesis within the intervertebral disc space between adjacent vertebral bodies.

Further objects, features, advantages, benefits, and aspects of the present invention will become apparent from the drawings and description contained herein.

DESCRIPTION OF THE PREFERRED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is hereby intended, and that any alterations and further modifications in the illustrated devices, and any further applications of the principles of the invention as illustrated herein are contemplated as would normally occur to one skilled in the art to which the invention relates.

Referring to FIGS. 1-4, shown therein is an articular disc prosthesis 20 according to one form of the present invention. The disc prosthesis 20 extends generally along a longitudinal axis L and includes an upper articular component 22a, a lower articular component 22b, and an articular ball 24 disposed between the upper and lower articular components 22a, 22b. The articular ball 24 defines a convex articular surface 25 and preferably has a spherical configuration. However, it should be understood that the articular ball 24 may take on other configurations as well, such as, for example, an elliptical or eccentric configuration.

The articular components 22a, 22b are configured substantially identical to one another. Therefore, the description and/or illustration of one of the articular components 22a, 22b applies equally to the other. In a preferred embodiment of the invention, the articular components 22a, 22b have a modular configuration. More specifically, each of the articular components 22a, 22b preferably includes an outer shell or endplate 26 and an inner articular cup or insert 28. As will be discussed in further detail below, the articular insert 28 can be removed from the endplate 26 and replaced with an insert of the same type or of a different type. The articular insert 28 is secured in position relative to the endplate 26 by a first set of fasteners 30. A second set of fasteners 32 is preferably included to engage the first set of fasteners to prevent the first set of fasteners 30 from loosening and backing out. In one embodiment of the invention, the fasteners 30, 32 are threaded set screws. However, it should be understood that other types and configurations of fasteners are also contemplated as would occur to one of ordinary skill in the art.

The upper and lower articular components 22a, 22b and the articular ball 24 cooperate to form an articulating joint that is sized and configured for disposition within an intervertebral disc space between adjacent vertebral bodies. Specifically, the convex outer surface 25 of the articular ball 24 cooperates with corresponding concave surfaces formed in the articular inserts 28 to provide relative articulating motion between the articular components 22a, 22b. In a preferred embodiment of the invention, such articulating motion includes both pivotal and rotational movement to maintain or restore motion substantially similar to normal bio-mechanical motion provided by a natural intervertebral disc.

Figure 1:
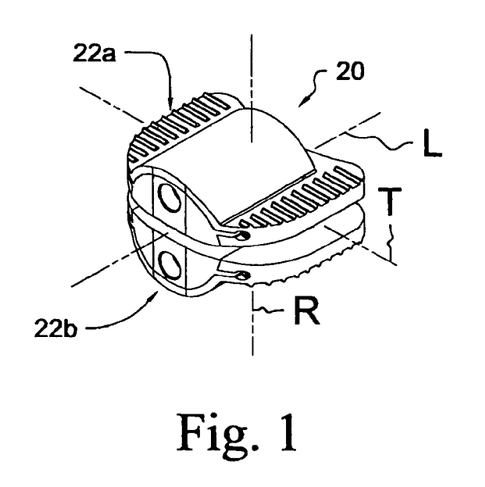
FIG. 1 is a perspective view of an articular disc prosthesis according to one form of the present invention.
Figure 2:
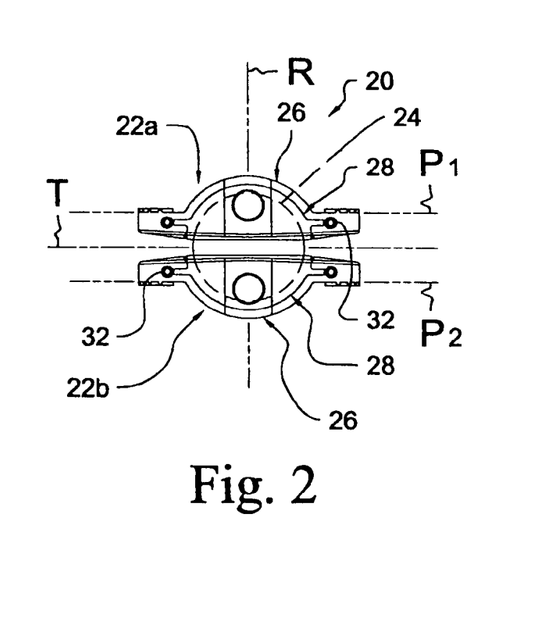
FIG. 2 is a front elevational view of the articular disc prosthesis illustrated in FIG. 1.
Figure 3:
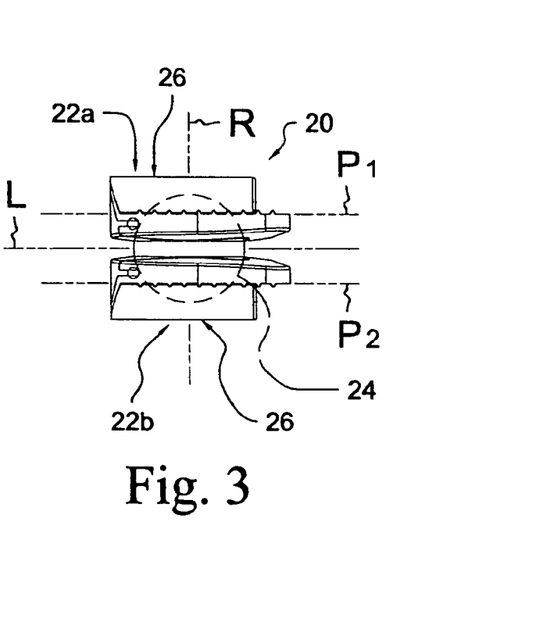
FIG. 3 is a side elevational view of the articular disc prosthesis illustrated in FIG. 1.

In one embodiment of the invention, the articular components 22a, 22b are permitted to rotate relative to one another about a rotational axis R. In another embodiment of the invention, the articular components 22a, 22b are permitted to pivot relative to one another about a number of axes, including lateral or side-to-side pivotal movement about the longitudinal axis L and anterior-posterior pivotal movement about a transverse axis T. In a further embodiment of the invention, the articular components 22a, 22b are permitted to pivot relative to one another about any axis which lies in a plane that intersects the longitudinal axis L and the transverse axis T. Although the disc prosthesis 20 has been illustrated and described as providing a combination of various articulating movements, it should be understood that other variations and combinations of articulating movements are also contemplated as falling within the scope of the present invention. It should also be understood that other types of articulating movement are also contemplated, such as, for example, relative translational or linear movement.

Although the various components of the articular disc prosthesis 20 may be formed from a wide variety of materials, following is a listing of various component materials according to one embodiment of the present invention. It should be understood, however, that the components of the disc prosthesis 20 may be formed of materials other than those specifically listed below, including any bio-compatible material that would be known to one of ordinary skill in the art or any other equivalent material.

The outer endplates 26 are preferably formed of a polymeric material, such as, for example, a polyaryletherketone polymer or polyethylene. In other embodiments of the invention, the outer endplates 26 may be formed of titanium, stainless steel, other types of metallic materials, or a ceramic material. The outer surfaces of the endplate 26 that are intended to be in direct contact with vertebral bone are preferably coated with a bone-growth promoting substance, such as, for example, a hydroxyapatite (HA) coating formed of calcium phosphate. The articular inserts 28 are preferably formed of a metallic material, such as, for example, cobalt-chrome-molybdenum metallic alloy (ASTM F-799 or F-75). In other embodiments of the invention, the articular inserts 28 may be formed of other types of metallic materials, such as, for example, titanium or stainless steel, a ceramic material, or a polymeric material. The articular ball 24 is preferably formed of a polymeric material, such as, form example, an ultra-high molecular weight polyethylene (UHMWPE). In another embodiment of the invention, the articular ball 24 may be cross-linked by radiation, by chemical means or by any other method know to those of skill in the art. In other embodiments of the invention, the articular ball 24 may be formed of titanium, stainless steel, other types of metallic materials, or a ceramic material. In one embodiment of the invention, the first set of fasteners 30 is formed of a polymeric material, such as, for example, a polyaryletherketone polymer. Preferably, the first set of fasteners 30 is formed of the same material as the endplates 26. In another embodiment of the invention, the second set of fasteners 32 is formed of a metallic material, such as, for example, cobalt-chrome-molybdenum metallic alloy. Preferably, the second set of fasteners 32 is formed of the same material as the articular inserts 28. In other embodiments of the invention, the first and second sets of fasteners 30, 32 may be formed of other types of materials, such as, for example, titanium, stainless steel, other types of metallic materials, a ceramic material, or a polymeric material.

Figure 5:
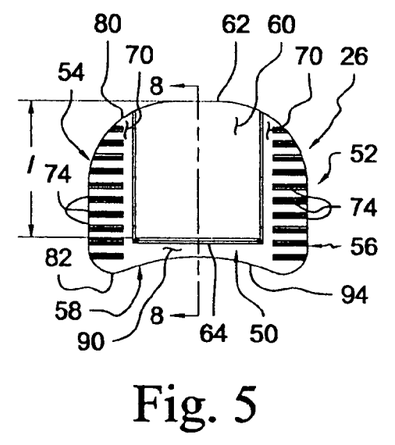
FIG. 5 is a top view of an endplate according to one embodiment of the present invention for use with the articular disc prosthesis illustrated in FIG. 1.

Referring to FIGS. 5-8, shown therein are various details regarding the configuration of the outer endplates 26. In one embodiment of the invention, the endplates 26 are each comprised of a central axial portion 50 and a lip portion 52 extending about a periphery of the axial portion 50. The peripheral lip portion 52 is comprised of a pair of flanges or wings 54, 56 extending laterally from the central portion 50, and a flange or lip 58 extending axially from the central portion 50. As shown in FIG. 5, the outer peripheral profile of the endplate 50 is preferably sized and shaped to substantially correspond to the size and shape of the vertebral endplate of an adjacent vertebra.

In one embodiment of the invention, the central axial portion 50 has a hemi-cylindrical configuration, including an outer surface 60 defining a convex lateral curvature extending along an axial length l. It should be understood, however, that the central axial portion 50 may take on other configurations, including other types of arcuate configurations, a rectangular configuration, or various types of polygonal configurations. It should also be understood that the convex outer surface 60 may take on other shapes, including an hemi-elliptical shape or other types of arcuate and/or polygonal configurations. The axial portion 50 includes an open axial end 62, a closed axial end 64, and a concave inner surface 66. The concave inner surface 66 defines a cavity 68 extending axially between the open and closed ends 62, 64. As will be discussed below, the cavity 68 is sized and shaped to receive a corresponding portion of the articular insert 28 therein. In one embodiment of the invention, the cavity 68 has a hemi-cylindrical configuration. However, it should be understood that the cavity 68 may take on other configurations as well, including other types of arcuate configurations, a rectangular configuration, or other types of polygonal configurations.

The lateral flanges 54, 56 each include an outwardly facing bearing surface 70 and an inwardly facing surface 72. In one embodiment of the invention, the outwardly facing bearing surface 70 is contiguous with the hemi-cylindrical outer surface 60 of the central axial portion 50. Similarly, the inwardly facing surface 72 is contiguous with the hemi-cylindrical inner surface 66 of the central axial portion 50. It should be understood, however, that other positions and orientations of the lateral flanges 54, 56 relative to the central axial portion 50 are also contemplated as falling within the scope of the present invention.

The outwardly facing bearing surface 70 preferably defines a number of anchor elements configured to engage vertebral bone. In one embodiment of the invention, the outwardly facing bearing surface 70 defines a number of projections or teeth 74. The teeth 74 are preferably triangular-shaped, defining pointed tips configured to bite into and securely grip vertebral bone. However, it should be understood that other configurations of the teeth 74 are also contemplated as would occur to one of skill in the art. It should also be understood that other types and configurations of anchor elements are also contemplated, such as, for example, spikes, protrusions, or various types of surface roughening features to aid in gripping vertebral bone to inhibit migration or expulsion of the disc prosthesis 20. In the illustrated embodiment of the invention, the teeth 74 extend laterally across a substantial portion of the width of flanges 54, 56 and are positioned intermittently along the length of the flange 54, 56. However, in another embodiment of the invention, the teeth 74 may extend along the length of the flange 54, 56 and may be positioned intermittently along the width of the flange 54, 56. It should also be understood that other positions and orientations of the teeth 74 are also contemplated as falling within the scope of the present invention.

In one embodiment of the invention, each of the lateral flanges 54, 56 has a first end 80, a second end 82, and an axial passage 84 extending from the first end 80 toward the second end 82. The axial passage 84 is disposed in communication with the hollow cavity 68 defined by the central axial portion 50, the purpose of which will be discussed below. In one embodiment, the axial passage 84 includes a circular portion 86 and a slot portion 88, with the slot portion 88 extending between the hollow cavity 68 and the circular portion 86. Internal threads 87 are preferably defined along a length of the circular portion 86 of axial passage 84 which are configured to threadingly receive the first and second sets of fasteners 30, 32.

The axial lip 58 includes an outwardly facing surface 90 and an inwardly facing surface 92. In one embodiment of the invention, the outwardly facing surface 92 is substantially flat. However, it should be understood the outwardly facing surface 92 could alternatively define a number of anchor elements configured to engage vertebral bone. The axial lip 58 includes an axially facing end surface 94 extending between the lateral flanges 54, 56. In one embodiment, the axially facing end surface 94 defines a recessed area 96 extending inwardly toward the central portion 50, the purpose of which will become apparent below. The recessed area 96 preferably has an arcuate configuration; however, other configurations are also contemplated as would occur to one of skill in the art.

Figure 6:
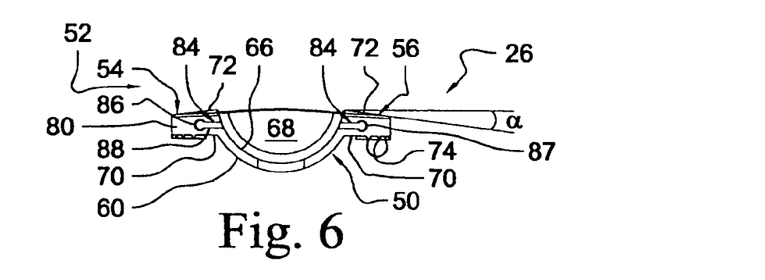
FIG. 6 is an end view of the endplate illustrated in FIG. 5.
Figure 7:
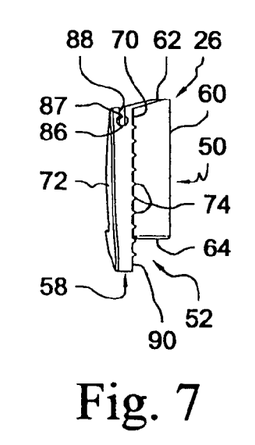
FIG. 7 is a side view of the endplate illustrated in FIG. 5.
Figure 8:
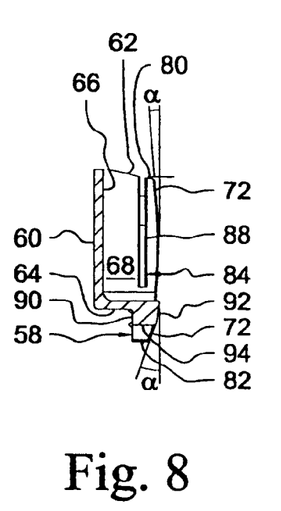
FIG. 8 is a sectional view of the endplate illustrated in FIG. 5, taken along line 8-8 of FIG. 5.

As illustrated in FIGS. 6 and 8, in one embodiment of the invention, the inwardly facing surfaces 72 of the lateral flanges 54, 56 preferably define an outward taper arranged at a taper angle α. The outward taper preferably extends in a lateral direction along the entire length of the flanges 54, 56 (as shown in FIG. 6). Additionally, at least the end portions of the inwardly facing surface 72 adjacent the ends 80, 82 are preferably tapered in an axial direction at a taper angle α. (as shown in FIG. 8). The inwardly facing surface 92 of the axial lip 58 also preferably defines an outward taper extending in an axial direction at a taper angle α. As should be appreciated, the inwardly facing surfaces 72, 92 of the lateral flanges 54, 56 and the axial lip 58 cooperate to define a substantially conically-shaped surface surrounding the central axial portion 50 and extending outwardly relative to the rotational axis R at the taper angle α. In this manner, relative pivotal movement between the articular components 22a, 22b is limited to a predetermined range of motion via abutment of the inwardly facing surfaces 72, 92 of one of the endplate 26 against the inwardly facing surfaces 72, 92 of the opposing endplate 26.

In one embodiment of the invention, the taper angle α falls within a range of between about 5 degrees and about 15 degrees, thereby limiting relative pivotal motion between the articular components 22a, 22b within a range of just over 10 degrees to just over 30 degrees. In a more specific embodiment, the taper angle α is about 7.5 degrees, thereby limiting relative pivotal motion between the articular components 22a, 22b to just over 15 degrees. It should be understood, however, that the taper angle α may take on other values to satisfy the specific articular requirements of the disc prosthesis 20, including taper angles α less than 5 degrees and greater than 15 degrees. It should also be understood that the taper angle α need not necessarily be uniform, but may instead be varied to limit relative pivotal motion between the articular components 22a, 22b within different ranges depending upon the particular pivotal axis about which the articular components 22a, 22b are being pivoted. In the illustrated embodiment of the invention, each of the endplates 26 of the articular components 22a, 22b define outwardly tapering surfaces 72, 92. However, it should be understood that in another embodiment of the invention, only one of the endplates 26 defines outwardly tapering surfaces 72, 92, with the other endplate 26 defining substantially flat inwardly facing surfaces 72, 92. In a further embodiment of the invention, both of the endplates 26 define substantially flat inwardly facing surfaces 72, 92.

Figure 9:
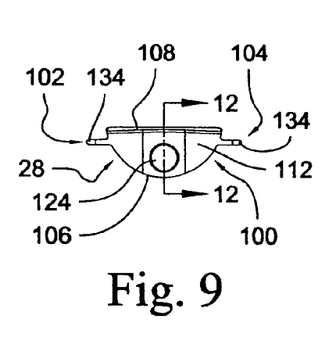
FIG. 9 is an end view of an insert according to one embodiment of the present invention for use with the articular disc prosthesis illustrated in FIG. 1.
Figure 10:
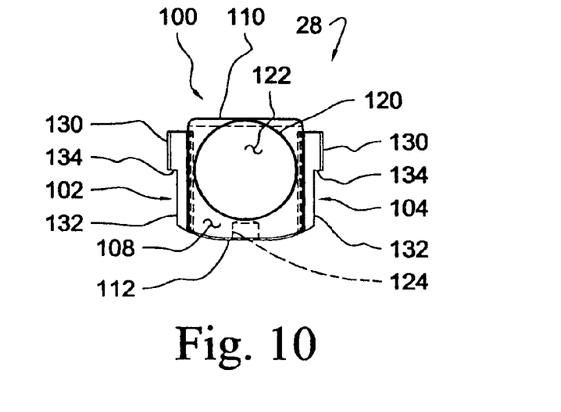
FIG. 10 is a top view of the insert illustrated in FIG. 9.
Figure 11:
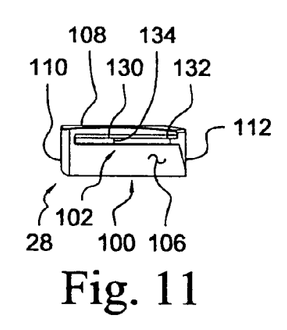
FIG. 11 is a side view of the insert illustrated in FIG. 10.
Figure 12:
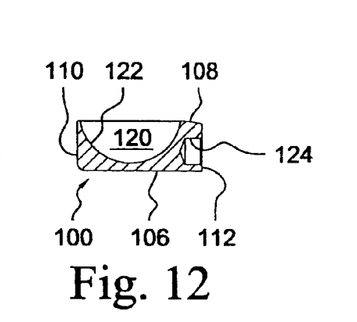
FIG. 12 is a sectional view of the insert illustrated in FIG. 9, taken along line 12-12 of FIG. 9.

Referring to FIGS. 9-12, shown therein are various details regarding the configuration of the inner articular inserts 28. In one embodiment of the invention, the articular inserts 28 are each comprised of a central body 100 and a pair of splines 102, 104 extending laterally from the central body 100. The central body 100 preferably has a shape and configuration that corresponds to the shape and configuration of the inner cavity 68 of the endplate 26. In one embodiment, the central body 100 includes a convex outer surface 106 that corresponds to the concave inner surface 66 of the endplate 26. The central body 100 also includes a relatively flat inner surface 108 disposed generally opposite the convex outer surface 106, and a pair of opposite axial end surfaces 110, 112. An axial opening 124 is preferably formed through the end surface 112 which is configured to receive a portion of an insertion instrument or tool therein (not shown). As illustrated in FIG. 10, the central body 100 has a hemi-cylindrical configuration that closely corresponds to the hemi-cylindrical configuration of the inner cavity 68 of the endplate 26. It should be understood, however, that the central body 100 may take on other configurations, including other types of arcuate configurations, a rectangular configuration, or various types of polygonal configurations.

The central body 100 includes a relatively large recess or socket 120 extending from the flat inner surface 108. The socket 120 defines a concave articular surface 122 that cooperates with the convex articular surface 25 of the ball 24 to provide articulating motion between the articular components 22a, 22b. More particularly, the ball 24 is at least partially disposed within the socket 120 such that the convex and concave articular surfaces 25, 122 are positioned in abutment to allow pivotal and rotational movement therebetween. In a preferred embodiment of the invention, the socket 120 is shaped and configured to closely correspond to the shape and configuration of the articular ball 24. In a one embodiment, the convex surface 25 of the ball 24 has a radius that is substantially equal to the radius of curvature of the concave surface 122 of socket 120. However, it should be understood that the radius of the articular ball 24 may be sized somewhat smaller than the radius of curvature of the socket 120. In one embodiment of the invention, the diameter of the articular ball 24 falls within a range of about 10 mm to about 30 mm. In a more specific embodiment, the diameter of the articular ball 24 is approximately 19 mm. Notably, since the area of abutment between the convex surface 25 of the articular ball 24 and the concave surface 122 of the socket 120 is relatively large, internal stresses within the disc prosthesis 20 are spread out over an increased surface area, thereby resulting in decreased wear and prolonged design life of the articular ball 24 and/or the articular inserts 28. Moreover, reducing internal stresses within the disc prosthesis 20 provides an opportunity to form the articular ball 24 and/or the articular inserts 28 from non-metallic materials, such as, for example, a polymeric material or a ceramic material.

Although the articular ball 24 and the socket 120 are illustrated as having generally smooth, uninterrupted abutting articular surfaces 25, 122, it should be understood that in other embodiments of the invention, either or both of the articular surfaces 25, 122 may define one or more surface depressions to facilitate removal of matter disposed between abutting portions of the articular surfaces. Such surface depressions may include, for example, grooves, channels, passages, openings, flattened areas, or dimples. Further details regarding the inclusion of surface depressions on either or both of the articular surfaces 25, 122 are disclosed in co-pending U.S. patent application Ser. No. 10/042,589, filed on Jan. 9, 2002 and entitled "Intervertebral Prosthetic Joint", the contents of which are hereby expressly incorporated by reference in their entirety.

The splines 102, 104 extending from the central body 100 are shaped and configured to be received within the axial passages 84 extending through the flanges 54, 56 of the endplate 26. Each of the splines 102, 104 preferably includes a first axial portion 130 and a second axial portion 132. The first axial portion 130 has a lateral width that is somewhat greater than the lateral width of the second axial portion 132 so as to form an axially facing shoulder 134, the purpose of which will be discussed below. As shown in FIGS. 6 and 9, the overall axial profile of the articular insert 28 substantially corresponds to that of the cavity 68 and the axial passages 84 defined within the endplate 26.

Referring once again to FIG. 4, the articular components 22a, 22b of the disc prosthesis 20 are assembled by engaging the articular inserts 28 with the endplates 26. More specifically, the articular insert 28 is axially inserted into the endplate 26, with the central body 100 and the splines 102, 104 of the insert 28 being slidably displaced along the central cavity 68 and the axial passages 84 of the endplate 26. The articular insert 28 is retained within the endplate 26 by way of the first set of set screws 30. The set screws 30 are threadingly engaged along the threaded portion 87 of the axial passage 84 until tightly engaged against the axial shoulder 134 of the splines 102, 104. The second set of set screws 32 are then threadingly engaged along the threaded portion 87 of the axial passage 84 until the set screws 32 engage the first set of set screws 30. The second set of set screws 32 serve to prevent the first set of set screws 30 from loosening and backing out. Once the articular components 22a, 22b have been assembled, the articular ball 24 is positioned within the sockets 120 defined by the articular inserts 28 to form the articulating disc prosthesis 20.

Figure 4:
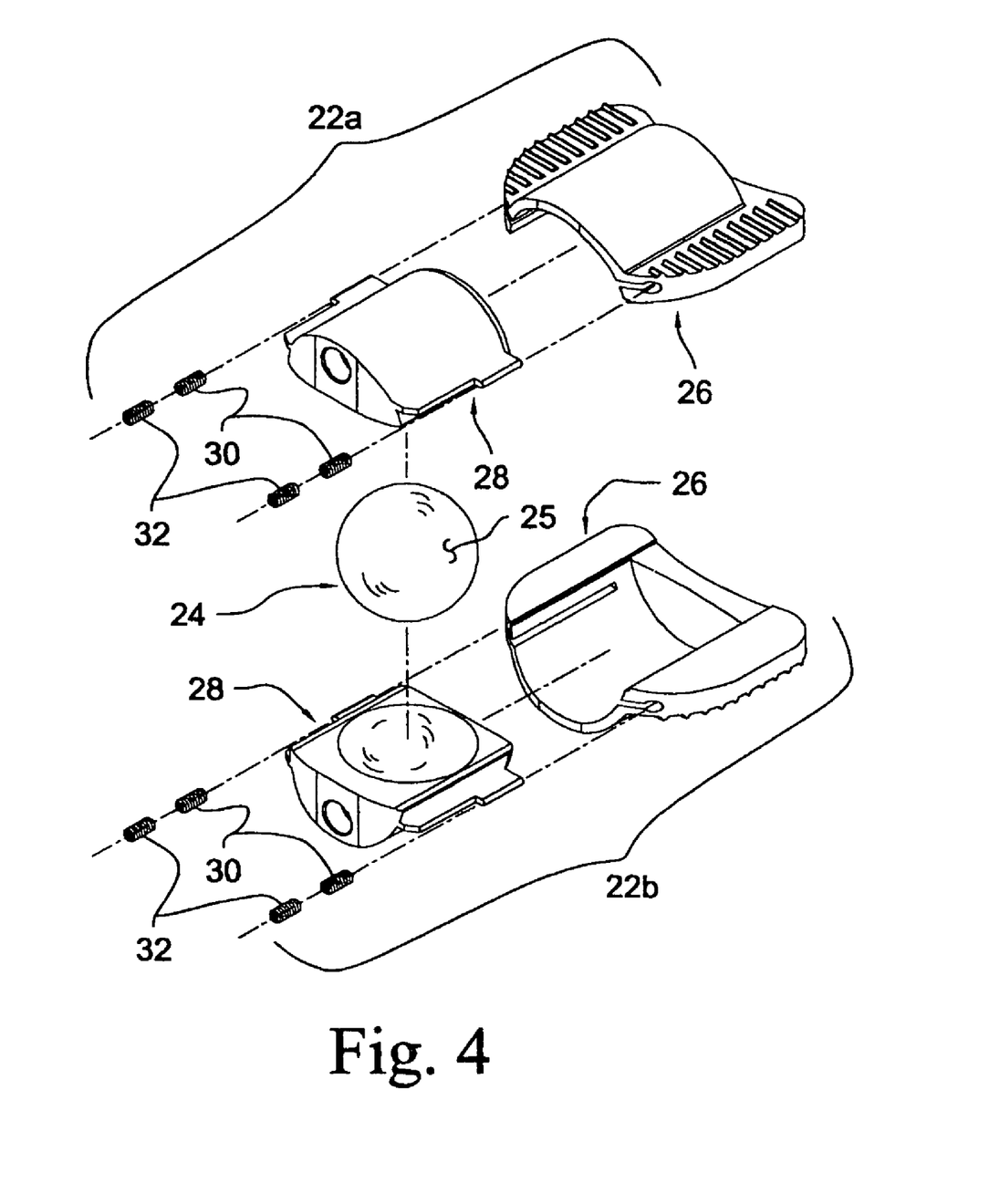
FIG. 4 is an exploded perspective view of the articular disc prosthesis illustrated in FIG. 1.

It should be appreciated that the modular nature of the disc prosthesis 20 offers several advantages. For example, if either of the articular components 22a, 22b or the articular ball 24 begins to malfunction or exhibits signs of wear, the disc prosthesis 20 can be easily disassembled by simply removing the set screws 30, 32 and sliding the articular inserts 28 and the articular ball 24 out from the endplates 26. Notably, removal of the articular inserts 28 and the articular ball 24 can be done in situ without having to remove the endplates 26 from the intervertebral disc space. This is particularly advantageous if bone on-growth onto the endplates 26 has already commenced, thereby avoiding having to break the bony engagement between the endplates 26 and adjacent vertebral bone.

The modular nature of the disc prosthesis 20 also allows the articulating characteristics and movements to be revised without having to remove the entire disc prosthesis 20 from the intervertebral disc space. Notably, the articular components 22a, 22b and the articular ball 24 originally implanted within the intervertebral disc space can be removed from the endplates 26 and replaced with different types/configurations of articular inserts 28 and/or a different articular ball 24 designed to provide the disc prosthesis 20 with modified articulating characteristics and movements. Once again, removal of the articular inserts 28 and the articular ball 24 can be done in situ without removing the endplates 26 from the intervertebral disc space. Additionally, the articular components 22a, 22b and the articular ball 24 may be removed from the endplates 26 and replaced with a rigid spacer element to provide rigid stabilization between the adjacent vertebrae, or by a semi-rigid or flexible spacer element to provide flexible stabilization between the adjacent vertebrae.

Figures 13, 14, 15:
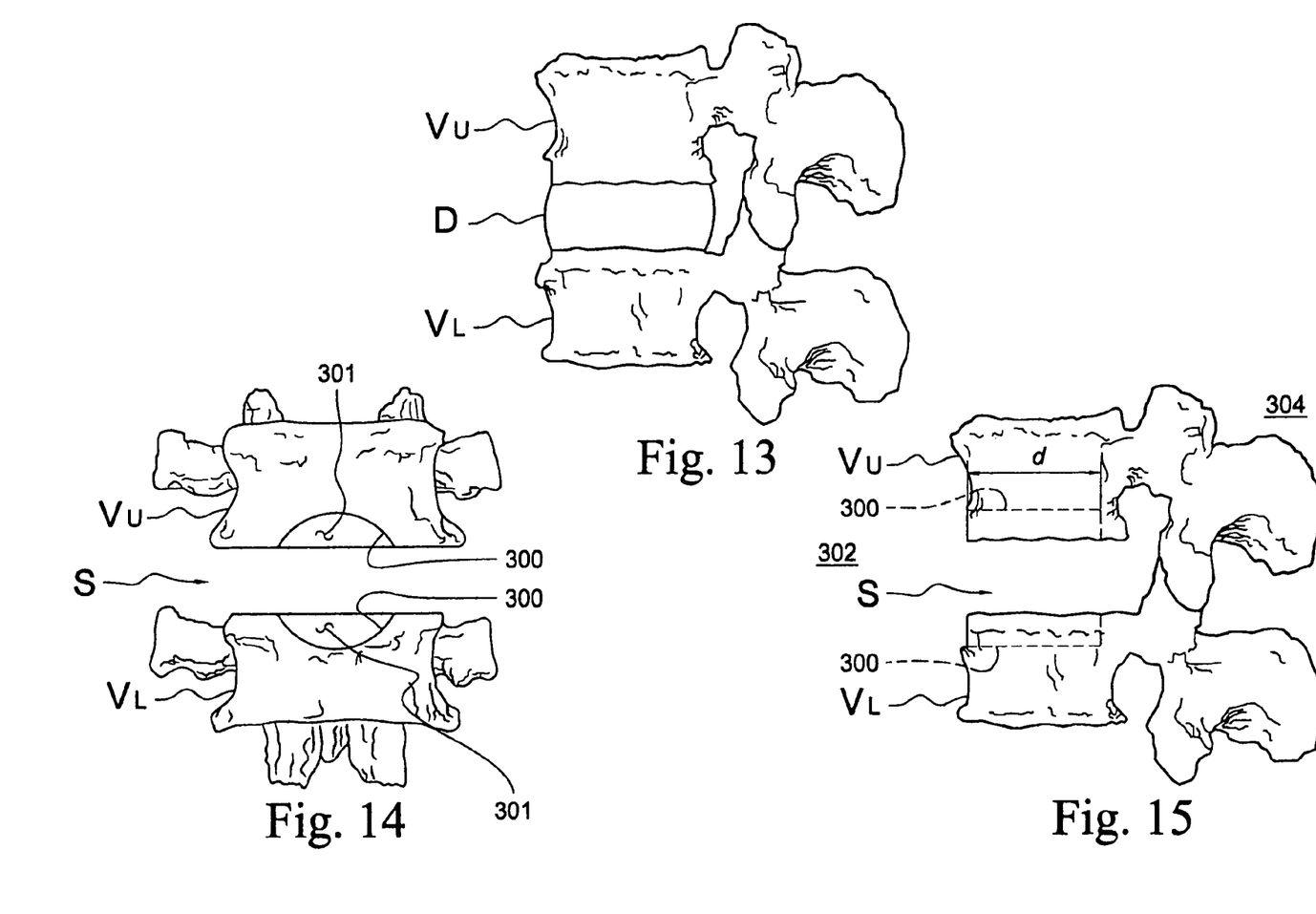
FIG. 13 is a lateral view of a portion of the spinal column, illustrating a pair of adjacent upper and lower vertebrae separated by a natural intervertebral disc.
FIG. 14 is an anterior view of the portion of the spinal column shown in FIG. 13, illustrating the removal of portions of the upper and lower vertebrae to accommodate insertion of the articular disc prosthesis illustrated in FIG. 1 therebetween.
FIG. 15 is a lateral view of the portion of the spinal column shown in FIG. 14.

Referring to FIG. 13, shown therein is a lateral view of a portion of the spinal column, illustrating a pair of adjacent upper and lower vertebrae $V_U$, $V_L$ separated by a natural intervertebral disc D. As discussed above, in cases where the natural intervertebral disc D is diseased or degenerated, most if not all of the natural disc D is typically removed via a discectomy or a similar surgical procedure, the details of which would be known to one of ordinary skill in the art.

As illustrated in FIGS. 14 and 15, removal of the diseased or degenerated disc D results in the formation of an intervertebral disc space S between the upper and lower vertebrae $V_U$, $V_L$. To accommodate for the insertion of the disc prosthesis 20 within the intervertebral disc space S, preparation of the upper and lower vertebrae $V_U$, $V_L$ is required. In one embodiment of the invention, the intervertebral space S is enlarged by forming elongate openings or recesses 300 along the inferior and superior portions of the upper and lower vertebrae $V_U$, $V_L$, respectively. The elongate recesses 300 preferably have a shape and configuration that substantially corresponds to the outer profile of the central axial portions 50 of the articular components 22a, 22b. In one embodiment, the elongate recesses 300 have a hemi-cylindrical shape; however, other shapes and configurations of the recesses 300 are also contemplated as would occur to one of skill in the art, including other types of arcuate configurations, a rectangular configuration, or other types of polygonal configurations.

In one embodiment of the invention, the elongate recesses 300 extend from an anterior side 302 of the vertebrae $V_U$, $V_L$ toward a posterior side 304 of the vertebrae $V_U$, $V_L$ to a predetermined depth d. In a preferred embodiment of the invention, the predetermined depth d of the elongate recesses 300 is approximately equal to or slightly greater than the length l of the central axial portions 50 of the articular components 22a, 22b. As will be discussed in further detail below, forming the recesses 300 at a predetermined depth d correspondingly controls the insertion depth of the disc prosthesis 20 to ensure proper positioning of the disc prosthesis 20 within the intervertebral disc space S. In one embodiment of the invention, the elongate recesses 300 are formed by reaming. However, other methods of forming the recesses 300 are also contemplated as would occur to one of ordinary skill in the art, such as, for example, by drilling, chiseling or curetting.

Figure 16:
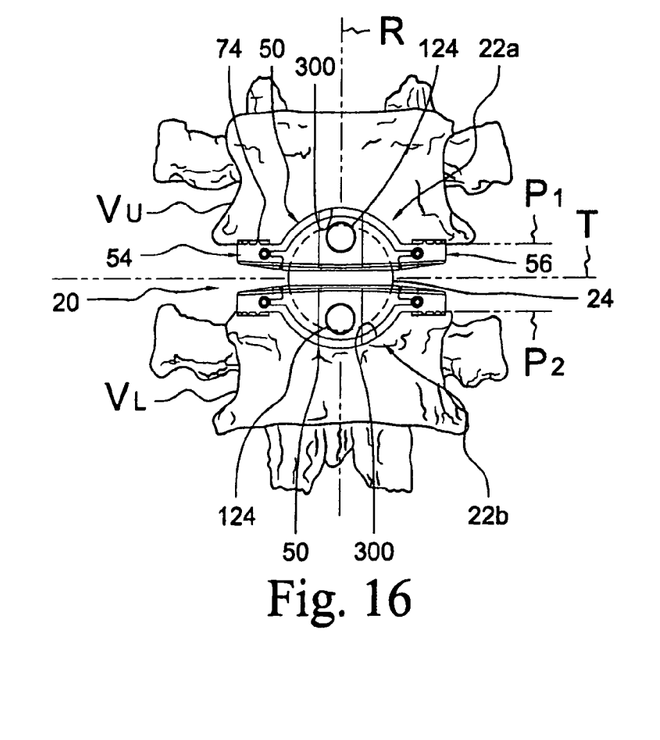
FIG. 16 is an anterior view of the portion of the spinal column shown in FIG. 14, illustrating implantation of the articular disc prosthesis between the upper and lower vertebrae.
Figure 17:
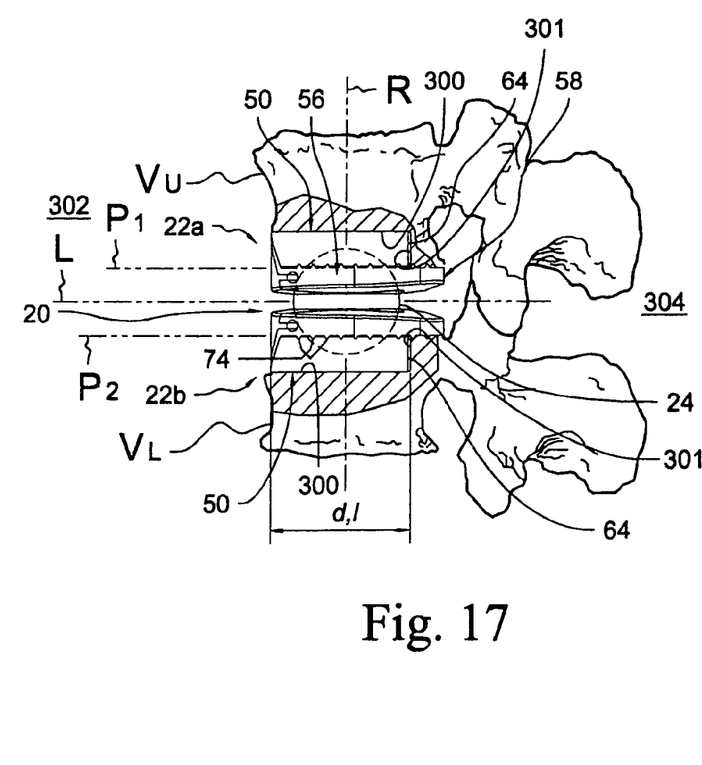
FIG. 17 is a partial sectional view of the portion of the spinal column shown in FIG. 16, illustrating implantation of the articular disc prosthesis between the upper and lower vertebrae.

Referring to FIGS. 16 and 17, following preparation of the upper and lower vertebrae $V_U$, $V_L$, the disc prosthesis 20 may then be implanted within the intervertebral disc space S. In one embodiment of the invention, implantation is accomplished by inserting the cylindrical axial portions 50 of the articular components 22a, 22b within the elongate recesses 300, with the bearing surfaces of the lateral flanges 54, 56 and the axial lip 58 facing the vertebral endplates of the upper and lower vertebrae $V_U$, $V_L$. The end surface 94 of the axial lip 58 faces a posterior direction, with the recessed area 96 defined by the axial lip 58 (FIG. 5) providing sufficient clearance to avoid encroachment into the area adjacent the spinal canal.

Prior to implantation of the disc prosthesis 20 within the intervertebral disc space S, the articular components 22a, 22b are preferably placed in a predetermined relationship with respect to one another. In one embodiment of the invention, an insertion instrument (not shown) may be used to position and secure the articular components 22a, 22b at a predetermined spacing and at a predetermined orientation relative to one another. The insertion instrument would maintain the articular components 22a, 22b at the predetermined spacing and orientation during manipulation of the disc prosthesis 20, and would be capable of selectively releasing the disc prosthesis 20 once properly positioned within the intervertebral disc space S. Such insertion instrument may include, for example, a pair of prongs adapted for insertion within the axial openings 124 formed in the articular inserts 28 of the articular components 22a, 22b.

As should be appreciated, the specific angular relationship between the articular component 22a, 22b is dictated by the geometry of the upper and lower vertebrae $V_U$, $V_L$ and the particular curvature or lordosis of the portion of the spinal column being treated. As such, the relative angular orientation of the planes $P_1$ and $P_2$ defined along the bearing surfaces 70 of the endplate flanges 54, 56 should correspond to the particular geometric configuration of the natural intervertebral disc D. As should also be appreciated, the distance between the planes $P_1$ and $P_2$ should be approximately equal to the height of the natural intervertebral disc D. Additionally, although the bearing surfaces 70 of the endplate flanges 54, 56 have been illustrated and described as having a substantially planar configuration, it should be understood that the bearing surfaces 70 may take on other configurations. For example, the bearing surfaces 70 may take on a curved or arcuate configuration that corresponds to the particular contour of the adjacent vertebral endplate against which the bearing surfaces 70 are engaged.

In one embodiment of the invention, the disc prosthesis 20 is inserted between the upper and lower vertebrae $V_U$, $V_L$ in a direction generally parallel to its longitudinal axis L, with the central axial portions 50 of the endplates 26 being axially displaced through the elongate recesses 300. Notably, since the central axial portions 50 are axially displaced through the preformed recesses 300, distraction of the upper and lower vertebrae $V_U$, $V_L$ to accommodate insertion of the disc prosthesis 20 is minimized, if not eliminated entirely. In the illustrated embodiment of the invention, the disc prosthesis 20 is inserted into the intervertebral disc space S via an anterior approach. However, it should be understood that the elongate recesses 300 may alternatively extend from the posterior side 304 of the vertebrae $V_U$, $V_L$ toward the anterior side 302 at a predetermined depth d to accommodate insertion of the disc prosthesis 20 into the intervertebral disc space S via a posterior approach. It should also understood that the elongate recesses 300 may alternatively extend from a first lateral side of the vertebrae $V_U$, $V_L$ toward an opposite lateral side of the vertebrae at a predetermined depth d to accommodate insertion of the disc prosthesis 20 into the intervertebral disc space S via a lateral approach.

As discussed above, the depth d of the elongate recesses 300 is approximately equal to or slightly greater than the length l of the central axial portions 50 of the endplates 26. Accordingly, precise position of the disc prosthesis 20 within the intervertebral disc space S is possible. Specifically, proper axial positioning of the disc prosthesis 20 is accomplished when the insertion ends 64 of the central axial portions 50 bottom out against the axially facing end surfaces 301 of the elongate recesses 300. Controlling the insertion depth of the disc prosthesis 20 results in more precise positioning to avoid over-insertion or under-insertion of the disc prosthesis 20. Additionally, disposition of the central axial portions 50 within the elongate recesses 300 substantially prevents lateral and/or rotational movement of the articular components 22a, 22b with respect to the upper and lower vertebrae $V_U$, $V_L$. The relatively large surface area of the central axial portions 50 contacting the upper and lower vertebrae $V_U$, $V_L$ also tends to minimize subsidence into the cancellous bone. Moreover, engagement of the bearing surfaces of the lateral flanges 54, 56 and the axial lip 58 against the upper and lower vertebrae $V_U$, $V_L$ tends to minimize subsidence of the disc prosthesis 20 into the cancellous bone.

Once the articular components 22a, 22b are properly positioned within the intervertebral disc space S, the axial lip 58 of the endplates 26 will bear against the posterior cortical rim of the upper and lower vertebrae $V_U$, $V_L$. Additionally, the anterior ends of the central axial portions 50 will bear against the anterior cortical rim of the upper and lower vertebrae $V_U$, $V_L$. Moreover, the lateral flanges 54, 56 may be configured to bear against the lateral cortical rim and/or the anterior cortical rim of the upper and lower vertebrae $V_U$, $V_L$. Such bearing engagement between the endplates 26 of the articular components 22a, 22b and the outer rim of the upper and lower vertebrae $V_U$, $V_L$ provides additional stabilization of the disc prosthesis 20 and tends to minimize subsidence. Additionally, the teeth 74 formed along the lateral flanges 54, 56 grip the bony endplates of the upper and lower vertebrae $V_U$, $V_L$ to resist migration of the disc prosthesis 20 and/or to prevent expulsion of the disc prosthesis 20 from the intervertebral disc space S.

The disc prosthesis 20 is initially maintained in position within the intervertebral disc space S relative to the upper and lower vertebrae $V_U$, $V_L$ via disposition of the central axial portions 50 within the elongate recesses 300 and by engagement of the teeth 74 against the bony vertebral endplates. However, over time the disc prosthesis 20 will be further secured to the upper and lower vertebrae $V_U$, $V_L$ via bony on-growth onto the surfaces of the articular components 22a, 22b that are in contact with vertebral bone tissue, particularly those surfaces which are in contact with metabolically active cancellous bone. Such bony on-growth provides further resistance to migration of the disc prosthesis 20 and possible expulsion from the intervertebral disc space S. It should be understood that other means for engaging the disc prosthesis 20 to the upper and lower vertebrae $V_U$, $V_L$ are also contemplated, such as, for example, bone screws, staples, an adhesive, or by other methods of engagement that would occur to one of ordinary skill in the art.

In use, the articular components 22a, 22b and the articular ball 24 cooperate to provide a ball-and-socket type joint that permits relative pivotal and rotational movement between the articular components 22a, 22b, which correspondingly permits relative pivotal and rotational movement between the upper and lower vertebrae $V_U$, $V_L$. More specifically, the spherical surface 25 of the articular ball 24 is slidably engaged against the concave surfaces 122 of the articular inserts 28. The resulting pivotal and rotational movement of the articular components 22a, 22b serves to maintain or restore articular motion to the portion of the spinal column being treated that is substantially similar to the normal biomechanical motion provided by a natural intervertebral disc D.

As shown in FIGS. 16 and 17, the unique geometry of the articular components 22a, 22b allows the use of a relatively large articular ball 24. As discussed above, use of an articular ball 24 having a large diameter increases the area of abutment between the convex surface 25 of the ball 24 and the concave surface 122 of the socket 120. As a result, internal stresses within the disc prosthesis 20 are reduced, thereby resulting in decreased wear and prolonged design life of the disc prosthesis 20. Use of a relatively large diameter articular ball 24 is made possible by the hemi-cylindrical central portions 50 of the endplates 26 which are positioned within the hemi-cylindrical recesses 300 formed along the upper and lower vertebrae $V_U, V_L$. Notably, this unique geometric design allows the use of an articular ball 24 having a diameter greater than the height of the natural intervertebral disc D. As a result, at least a portion of the abutting articular surfaces 25, 122 of the ball 24 and the articular insert 28 is positioned beyond the intervertebral disc space defined between the planes $P_1$ and $P_2$ extending along the bearing surfaces 70 of the endplate flanges 54, 56.

Although the disc prosthesis 20 has been illustrated and described as including a pair of articular components 22a, 22b having a separate articular ball 24 disposed therebetween, in an alternative embodiment of the invention the articular ball 24 may be replaced by a protrusion formed integral with one of the articular inserts 28. In this alternative embodiment, the protrusion extending from one of the articular inserts 28 would be at least partially disposed within the socket 120 defined by the opposing articular insert 28. A convex articular surface defined by the protrusion would cooperate with the concave articular surfaces 122 defined by the opposing socket 120 to provide pivotal and rotational articulating motion between the articular components 22a, 22b.

Additionally, although the devices and methods illustrated and described above are particularly useful in treating the lumbar region of the spine, it should nevertheless be understood that the present invention is also applicable to other portions of the spine, including the cervical or thoracic regions of the spine.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. An articular disc prosthesis for disposition between a first vertebra and a second vertebra, comprising:
   a first articular component including a first cylindrical portion and a first flange portion extending laterally therefrom and defining a first vertebral bearing surface adapted to engage the first vertebra; and
   a second articular component including a second cylindrical portion and a second flange portion extending laterally therefrom and defining a second vertebral bearing surface adapted to engage the second vertebra; and
   an articulating joint configured to provide articulating motion between said first and second articular components; and
   wherein said first and second cylindrical portions each extend generally along a longitudinal axis from a first axial end portion to an opposite second axial end portion, said first and second cylindrical portions each including a hemi-cylindrical outer surface extending along an axial length of said cylindrical portions from said first axial end portion to said second axial end portion.

2. The articular disc prosthesis of claim 1, wherein said first articular component includes a first pair of flange portions extending laterally from said first cylindrical portion in generally opposite directions, and wherein said second articular component includes a second pair of flange portions extending laterally from said second cylindrical portion in generally opposite directions.

3. The articular disc prosthesis of claim 2, wherein said first cylindrical portion defines a convex lateral curvature extending between said first pair of flange portions and along said axial length of said first cylindrical portion from said first axial end portion to said second axial end portion, and wherein said second cylindrical portion defines a convex lateral curvature extending between said second pair of flange portions and along said axial length of said second cylindrical portion from said first axial end portion to said second axial end portion.

4. The articular disc prosthesis of claim 1, wherein said first vertebral bearing surface is substantially planar and is defined along a first plane and said second vertebral bearing surface is substantially planar and is defined along a second plane, said first and second planes defining a space therebetween; and wherein at least one of said first and second articular components includes a concave articular surface that cooperates with a corresponding convex articular surface to provide said articulating joint, at least a portion of said concave articular surface positioned beyond said space between said first and second planes and through a corresponding one of said first and second planes when said first and second planes are arranged parallel with one another.

5. The articular disc prosthesis of claim 4, wherein each of said first and second articular components includes a concave articular surface that cooperates with said corresponding convex articular surface to provide said articulating joint, at least a portion of each of said concave articular surface positioned beyond said space between said first and second planes and through a corresponding one of said first and second planes when said first and second planes are arranged parallel with one another.

6. The articular disc prosthesis of claim 5, further comprising an articular ball defining a spherical outer surface positioned between said first and second articular components, said spherical outer surface of said articular ball cooperating with each of said concave articular surfaces to provide said articulating joint.

7. The articular disc prosthesis of claim 4, wherein a distance between said first and second planes is approximately equal to a height of a natural intervertebral disc space between the first and second vertebrae.

8. The articular disc prosthesis of claim 1, wherein said articulating joint comprises an articular ball defining a spherical outer surface positioned within an articular socket defined by each of said first and second articular components.

9. The articular disc prosthesis of claim 1, wherein said hemi-cylindrical outer surfaces extend along an entire axial length of said first and second cylindrical portions, respectively.

10. An articular disc prosthesis for disposition between a first vertebra and a second vertebra, comprising:
    a first articular component including a first articular portion and a first flange portion extending laterally therefrom and defining a first vertebral bearing surface adapted to engage an endplate of the first vertebra;
    a second articular component including a second articular portion and a second flange portion extending laterally therefrom and defining a second vertebral bearing surface adapted to engage an endplate of the second vertebra; and
    an articulating joint configured to provide articulating motion between said first and second articular components, at least a portion of said articulating joint positioned beyond a space between said first and second vertebral bearing surfaces; and wherein each of said first and second articular portions has a hemi-cylindrical shape and each extends generally along a longitudinal axis from a first axial end portion to an opposite second axial end portion, said first and second articular portions each including a hemi-cylindrical outer surface extending along an axial length of said articular portions from said first axial end portion to said second axial end portion.

11. The articular disc prosthesis of claim 10, wherein said hemi-cylindrical outer surfaces extend along an entire axial length of said first and second articular portions, respectively.

12. The articular disc prosthesis of claim 10, wherein said first vertebral bearing surface defined by said first flange portion is substantially planar and is defined along a first plane;

wherein said second vertebral bearing surface defined by said second flange portion is substantially planar and is defined along a second plane; and wherein said at least a portion of said articulating joint is positioned beyond said first and second planes and through a corresponding one of said first and second planes when said first and second planes are arranged parallel with one another.

13. An articular disc prosthesis for disposition between a first vertebra and a second vertebra, comprising:

a first articular component including a first articular portion and a first flange portion extending laterally therefrom and defining a first vertebral bearing surface adapted to engage an endplate of the first vertebra, said first vertebral bearing surface is substantially planar and is defined along a first plane;

a second articular component including a second articular portion and a second flange portion extending laterally therefrom and defining a second vertebral bearing surface adapted to engage an endplate of the second vertebra, said second vertebral bearing surface is substantially planar and is defined along a second plane; and an articulating joint configured to provide articulating motion between said first and second articular components, at least a portion of said articulating joint positioned beyond a space between said first and second planes and through a corresponding one of said first and second planes when said first and second planes are arranged parallel with one another;

wherein each of said first and second articular portions defines an outer lateral curvature, and wherein each of said first and second articular portions has a hemi-cylindrical shape and each extends generally along a longitudinal axis from a first axial end portion to an opposite second axial end portion, said first and second articular portions each including a hemi-cylindrical outer surface extending along an axial length of said articular portions from said first axial end portion to said second axial end portion.

14. The articular disc prosthesis of claim 13, wherein said first articular component includes a first pair of flange portions extending laterally from said first articular portion in generally opposite directions away from said first articular component, said first pair of flange portions each defining a vertebral bearing surface extending along said first plane;

wherein said second articular component includes a second pair of flange portions extending laterally from said second articular portion in generally opposite directions away from said second articular component, said second pair of flange portions each defining a vertebral bearing surface extending along said second plane.

15. The articular disc prosthesis of claim 14, wherein said first articular portion defines a convex lateral curvature extending between said first pair of flange portions, and wherein said second articular portion defines a convex lateral curvature extending between said second pair of flange portions.

16. The articular disc prosthesis of claim 13, wherein a distance between said first and second planes is approximately equal to a height of a natural intervertebral disc space between the first and second vertebrae.

* * * * *